(12) United States Patent
Kerl et al.

(10) Patent No.: US 10,117,825 B2
(45) Date of Patent: Nov. 6, 2018

(54) OXIDATION COLORING COMPOSITION WITH PROTEIN-SILOXANE POLYMERS

(71) Applicant: Henkel AG & Co. KGaA, Duesseldorf (DE)

(72) Inventors: Sylvia Kerl, Hamburg (DE); Camille Grosjacques, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/454,679

(22) Filed: Mar. 9, 2017

(65) Prior Publication Data

US 2017/0172896 A1    Jun. 22, 2017

Related U.S. Application Data

(63) Continuation of application No. PCT/EP2015/068879, filed on Aug. 18, 2015.

(30) Foreign Application Priority Data

Sep. 9, 2014    (DE) .................. 10 2014 218 005

(51) Int. Cl.

| | |
|---|---|
| *A61Q 5/10* | (2006.01) |
| *A61K 8/891* | (2006.01) |
| *A61K 8/64* | (2006.01) |
| *A61K 8/73* | (2006.01) |
| *A61K 8/34* | (2006.01) |
| *A61K 8/46* | (2006.01) |
| *A61K 8/37* | (2006.01) |
| *A61K 8/44* | (2006.01) |
| *A61K 8/41* | (2006.01) |
| *A61K 8/23* | (2006.01) |
| *A61K 8/97* | (2017.01) |
| *A61K 8/55* | (2006.01) |
| *A61K 8/49* | (2006.01) |
| *A61K 8/19* | (2006.01) |
| *A61K 8/86* | (2006.01) |
| *A61K 8/92* | (2006.01) |
| *A61K 8/22* | (2006.01) |
| *A61Q 5/06* | (2006.01) |

(52) U.S. Cl.
CPC ............... *A61K 8/891* (2013.01); *A61K 8/19* (2013.01); *A61K 8/22* (2013.01); *A61K 8/23* (2013.01); *A61K 8/342* (2013.01); *A61K 8/345* (2013.01); *A61K 8/347* (2013.01); *A61K 8/37* (2013.01); *A61K 8/375* (2013.01); *A61K 8/41* (2013.01); *A61K 8/411* (2013.01); *A61K 8/418* (2013.01); *A61K 8/442* (2013.01); *A61K 8/463* (2013.01); *A61K 8/466* (2013.01); *A61K 8/4926* (2013.01); *A61K 8/55* (2013.01); *A61K 8/645* (2013.01); *A61K 8/73* (2013.01); *A61K 8/86* (2013.01); *A61K 8/925* (2013.01); *A61K 8/97* (2013.01); *A61Q 5/065* (2013.01); *A61Q 5/10* (2013.01); *A61K 2800/882* (2013.01)

(58) Field of Classification Search
CPC ........ A61K 8/891; A61K 8/645; A61K 8/463; A61K 8/345; A61K 8/442; A61K 8/41; A61K 8/97; A61K 8/466; A61K 8/55; A61K 8/19; A61K 8/86; A61K 8/925; A61K 8/37; A61K 8/22; A61K 2800/882; A61Q 5/10; A61Q 5/065
See application file for complete search history.

(56) References Cited

U.S. PATENT DOCUMENTS

| | | |
|---|---|---|
| 5,412,074 A | 5/1995 | Jones et al. |
| 2003/0235554 A1 | 12/2003 | Chahal |
| 2013/0156716 A1* | 6/2013 | Yontz .................. A61K 8/4973 424/70.6 |

FOREIGN PATENT DOCUMENTS

| | | |
|---|---|---|
| JP | 2001/151643 | 6/2001 |
| JP | 2002/265339 | 9/2002 |
| JP | 2004/075630 | 3/2004 |
| WO | 2014/143667 A1 | 9/2014 |

OTHER PUBLICATIONS

STIC Search Report dated May 5, 2017.*
PCT International Search Report (PCT/EP2015/068879) dated Oct. 13, 2015.
Andrews P., "Estimation of the Molecular Weights of Proteins by Sephadex Gel-Filtration"; Biochem. J., 1964, 91, 222-233.
G. Schuster und A. Domsch, Seifen Öle Fette Wachse 108, (1982) 177.
N. Geria_Formulation of stick antiperspirants and deodorant; Cosmetics & Toiletries, 1984, vol. 99, 55-66.
H. W. Steisslinger, Parf.Kosm. 72, (1991) 556.
F. Aurich et al., Tens.Surf.Det. 29, (1992) 389.
Liu X. M. et. al., "Comparative Studies of Poly(DimethylSiloxanes) Using Automated GPC-MALDI-TOF MS and On-Line GPC-ESI-TOF MS"; Am. Soc. Mass. Spectrom., 2003, 14, 195-202.
Doering Thomas et al, "Super mild oxidation coloring: preventing hair damage at the molecular level", IFSCC Magazine, Allured Pub., Bd. 10, Nr. 4, Jan. 1, 2007.
XP002745115, "Root Rehab Emergency Retouch Kit", Sep. 2009.

\* cited by examiner

*Primary Examiner* — Eisa B Elhilo
(74) *Attorney, Agent, or Firm* — James J. Cummings

(57) ABSTRACT

A cosmetic agent for dyeing keratinous fibers, especially human hair, includes at least one specific protein-siloxane polymer and at least one oxidation dye precursor and/or a direct dye, where the use of the at least one protein-siloxane polymer leads to improved care of the keratinous fibers. A corresponding packaging unit (kit of parts) and a method for dyeing keratinous fibers include the cosmetic agent. Lastly, the cosmetic agent is used to care for keratinous fibers with an enhanced care effect.

15 Claims, No Drawings

US 10,117,825 B2

OXIDATION COLORING COMPOSITION WITH PROTEIN-SILOXANE POLYMERS

FIELD OF THE INVENTION

The present invention relates to cosmetic agents for dyeing keratinous fibers, which include protein-siloxane polymers.

The present invention further relates to a packaging unit (kit-of-parts) containing a cosmetic agent according to the present invention, as well as an oxidizing agent preparation.

The present invention furthermore relates to a method for dyeing keratinous fibers with the use of a cosmetic agent according to the present invention as well as an oxidizing agent preparation.

In addition, the present invention relates to the use of a cosmetic agent according to the present invention to enhance the care of keratinous fibers.

Finally, the present invention relates to the use of a packaging unit according to the present invention to produce a cosmetic agent for altering the color of keratinous fibers with enhanced care for the keratinous fibers.

BACKGROUND OF THE INVENTION

Altering the shape and color of hair represents an important area of modern cosmetics. The appearance of the hair may thus be adapted both to current fashion trends and to the consumer's individual preferences. The fashionable use of colors for hairstyles or the layering of greyed or white hair with fashionable or natural color tones is typically done with color-changing agents. These agents should, in addition to high dyeing power, have additional properties such as, for example, increasing the volume of the hair.

Different dyeing systems are known in the prior art for providing color-altering cosmetic agents, in particular for the skin or keratin-containing fibers, such as, for example, human hair.

For permanent, intense colorations having appropriate fastness properties, so-called oxidation dyes are used. Such dyes typically include oxidation dye precursors, so-called developer components and coupler components. The developer components constitute the actual dyes, under the influence of oxidizing agents or atmospheric oxygen among one another or under coupling with one or more coupler components. Oxidation dyes are characterized by excellent, long-lasting dyeing results. For natural-looking colorations, however, it is typically necessary to use a mixture of a greater number of oxidation dye precursors; in many cases, direct dyes are also used for shading.

Coloring or tinting agents containing so-called substantive dyes as the coloring component are typically used for temporary colors. These are dye molecules that are taken up directly into the substrate and do not require an oxidative process to form the color. One example of these dyes is henna, which has been known since ancient times as a means for dyeing the body and hair. These colorations are generally much more sensitive to shampooing than oxidative coloration, so that an often unwanted shift in shade or a visible, uniform color loss occurs much earlier.

Finally, another dyeing method has attracted considerable attention. In this method, precursors of the natural hair dye melanin are applied to the substrate, e.g., hair; these then form analogs of natural dyes in the hair, within the framework of oxidative processes. In such methods, for example, 5,6-dihydroxyindoline is used as a dye precursor. In particular, multiple applications of agents comprising 5,6-dihydroxyindoline make it possible to restore the natural hair color of people with greyed hair. The coloration can then take place with atmospheric oxygen as the only oxidizing agent, so that additional oxidizing agents can be forgone. In people with originally medium-blond to brown hair, 5,6 dihydroxyindoline can be used as the sole dye precursor. For use in people with originally red and, in particular, dark to black hair colors, however, satisfactory results can usually only be achieved with concomitant use of further dye components, in particular specific oxidation dye precursors.

The dyes known in the prior art, however, do not always lead to the desired high coloring performance, or have additional desired properties, e.g., an improved care effect.

The present invention therefore addresses the problem of providing a cosmetic agent for dyeing keratinous fibers, which prevents or at least mitigates the shortcomings of the prior art and results in improved care for the keratinous fibers dyed with these agents.

Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is therefore a cosmetic agent for altering the color of keratinous fibers, comprising, in a cosmetically acceptable carrier, a) at least one compound selected from the group consisting of oxidation dye precursors, direct dyes, and mixtures thereof, and b) at least one protein-siloxane polymer containing at least one structural unit of formula (I) and/or at least one structural unit of formula (II)

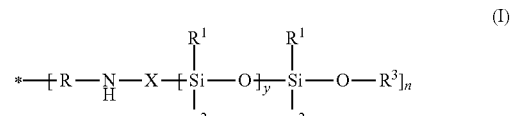

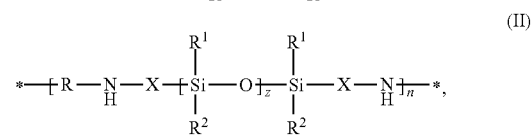

where:

R stands for a hydrolyzed protein residue having at least one NH2 group;

X stands for a group *—CH2—CH(OH)—CH2—O—(CH2)3—* or *—CO—CH(CH2COOH)—CH—(CH2)3—*; R1 and R2 each independently of one another stand for a methyl group, a hydroxy group, an alkoxy group having 1 to 6 carbon atoms in the alkyl chain, a residue of formula (IIIa)

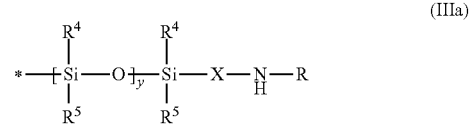

or (IIIb)

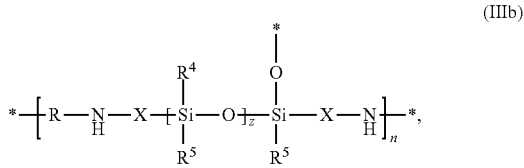

where R4 and R5 each independently of one another stand for a methyl group, a hydroxy group, or an alkoxy group having 1 to 6 carbon atoms in the alkyl chain;
R3 stands for a hydrogen atom or a group X—H;
n stands for an integer 1 to 101;
y stands for an integer 0 to 1,000, preferably 0 to 500, in particular 0 to 100; and
z stands for an integer 1 to 1,000, preferably 1 to 500, in particular 1 to 100.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now surprisingly been found that adding at least one protein-siloxane polymer to cosmetic agents for dyeing keratinous fibers results in an improved care effect, without adversely affecting the dyeing performance of the cosmetic agents according to the present invention or the shelf life thereof.

The term "keratinous fibers or even keratin fibers" is understood according to the present invention to mean fur, wool, feathers, and human hair. Within the framework of the present invention, it is especially preferable when the cosmetic agents are used to dye human hair.

The term "combability" within the framework of the present invention is understood to mean both the combability of the fibers when wet and the combability of the fibers when dry.

The term "protein-siloxane polymers" is understood according to the present invention to mean polymers that include both protein residues and siloxane units and can be obtained by reacting a protein with an organofunctional siloxane. Protein residues are understood in this context to mean chemical compounds that constitute condensation products of amino acids amide-linked by peptide bonds and are bonded to the siloxane backbone via a spacer X. The number of amino acids in the protein residues is preferably at least 5 and at most 1,000 amino acids. The term "protein residue" according to the present invention is also understood to mean hydrolysates of proteins containing protein fractions with different amino acid sequences and molecular weights. The protein-siloxane polymers may be linear or crosslinked. Crosslinked polymers within the framework of the present invention exist if the groups R1 and/or R2 stand for a residue of formula (IIIb).

Moreover, within the framework of the present invention, the term "fatty alcohols" is understood to mean aliphatic, long-chain, monohydric primary alcohols which have unbranched hydrocarbon residues comprising 6 to 30 carbon atoms. The hydrocarbon residues may be saturated or mono- or polyunsaturated.

Finally, within the framework of the present invention, the term "fatty acids" is understood to mean aliphatic monocarboxylic acids that have an unbranched carbon chain and comprise hydrocarbon residues having 6 to 30 carbon atoms. The hydrocarbon residues may be either saturated or mono- or polyunsaturated.

The setting forth of the total amount in relation to the components of the cosmetic agent refers presently—unless otherwise indicated—to the total amount of active substance of the respective component. Furthermore, the setting forth of the total amount in relation to the components of the cosmetic agent refers—unless otherwise indicated—to the total weight of the oxidizing agent-free cosmetic agent according to the present invention.

The cosmetic agents according to the present invention include a cosmetic carrier. Preferably according to the present invention, the cosmetic carrier is aqueous, alcoholic, or aqueous-alcoholic. Within the framework of the present invention, for example, creams, emulsions, gels, or surfactant-containing foaming solutions, such as shampoos, foam aerosols, or other preparations suitable for use on hair can be used. An aqueous carrier within the sense of the present invention includes at least 30 wt %, in particular at least 50 wt % water, relative to the total weight of the cosmetic agent.

Aqueous-alcoholic carriers are understood, within the meaning of the present invention, to mean water-containing compositions containing a C1-C4 alcohol in a total amount of 3 to 90 wt % relative to the total weight of the cosmetic agent, in particular ethanol or isopropanol.

The cosmetic agents according to the present invention may additionally include further organic solvents, for example, methoxybutanol, ethyl diglycol, 1,2-propylene glycol, n-propanol, n-butanol, n-butylene glycol, glycerol, diethylene glycol monoethyl ether, and diethylene glycol mono-n-butyl ether. All water-soluble organic solvents are preferred therein, wherein the solvent is included in a total amount of 0.1 to 30 wt %, preferably 1 to 20 wt %, in particular 2 to 10 wt %, relative to the total weight of the cosmetic agent.

The cosmetic agent according to the present invention includes, as the first essential component a), a compound selected from the group consisting of oxidation dye precursors (ODPs), direct dyes (DDs), and mixtures thereof.

In a preferred embodiment, cosmetic agents according to the present invention include at least one oxidation dye precursor.

Oxidation dye precursors can be divided into two categories—so-called developer components and coupler components—by the reaction behavior thereof. Developer components are able to form the actual dye on their own. They may therefore be included as the sole compounds in the cosmetic agent according to the present invention. In a preferred embodiment, the cosmetic agents according to the present invention therefore include at least one oxidation dye precursor of the developer type. It may, however, also be provided within the framework of the present invention that the cosmetic agents according to the present invention include at least one oxidation dye precursor of the coupler type. Especially favorable results with regard to the coloration of keratinous fibers are obtained when the cosmetic agents according to the present invention include at least one oxidation dye precursor of the developer type and at least one oxidation dye precursor of the coupler type.

The developer and coupler components are typically used in a free form. With substances that have amino groups, however, it may be preferable to use the salt forms thereof, in particular in the form of the hydrochlorides and hydrobromides or the sulfates.

Preferred according to the present invention are cosmetic agents that include the developer and/or coupler components in a total amount—in each case—of 0.001 to 10 wt %, preferably 0.01 to 8 wt %, preferably 0.1 to 5 wt %, in particular 0.5 to 3 wt %, relative to the total weight of the cosmetic agent.

In another preferred embodiment, the cosmetic agent according to the present invention is therefore characterized by containing an oxidation dye precursor of the developer and/or coupler type in a total amount of 0.001 to 10 wt %, preferably 0.01 to 8 wt %, preferably 0.1 to 5 wt %, in particular 0.5 to 3 wt %, relative to the total weight of the cosmetic agent.

Suitable oxidation dye precursors of the developer type are, for example, p-phenylenediamine and derivatives thereof. Preferred p-phenylenediamines are selected from one or more compounds of the group consisting of p-phenylenediamine, p-tolylenediamine, 2-chloro-p-phenylenediamine, 2,3-dimethyl-p-phenylenediamine, 2,6-dimethyl-p-phenylenediamine, N,N-bis-(2-hydroxyethyl)-p-phenylenediamine, 2-(2-hydroxyethyl)-p-phenylenediamine, 2-(1,2-dihydroxyethyl)-p-phenylenediamine, N-(2-hydroxypropyl)-p-phenylenediamine, N-(4'-aminophenyl)-p-phenylenediamine, 2-methoxymethyl-p-phenylenediamine, N-phenyl-p-phenylenediamine, 2-(2-hydroxyethyloxy)-p-phenylenediamine, and N-(4-amino-3-Methyl-phenyl)-N-[3-(1H-imidazol-1-yl) propyl] amine, and physiologically acceptable salts thereof.

It may be furthermore preferred, according to the present invention, to use compounds containing at least two aromatic nuclei substituted with amino and/or hydroxy groups as the developer component. Preferred binuclear developer components are selected from N,N'-bis-(2-hydroxyethyl)-N,N'-bis-(4'-aminophenyl)-1,3-diaminopropan-2-ol, N,N'-bis(4-aminophenyl)-1,4-diazacycloheptane, bis-(2-hydroxy-5-aminophenyl) methane, and physiologically acceptable salts thereof.

Furthermore, it may be preferred according to the present invention to use a p-aminophenol derivative or one of the physiologically acceptable salts thereof as the developer component. Preferred p-aminophenols are p-aminophenol, N-methyl-p-aminophenol, 4-amino-3-methylphenol, 4-amino-2-aminomethylphenol, 4-amino-2-(1,2-dihydroxyethyl) phenol, 4-amino-2-diethylaminomethyl) phenol, and physiologically acceptable salts thereof.

Furthermore, the developer component may be selected from o-aminophenol and derivatives thereof, preferably from 2-amino-4-methylphenol, 2-amino-5-methylphenol, 2-amino-4-chlorophenol, and/or physiologically acceptable salts thereof.

The developer component may also be selected from heterocyclic developer components such as pyrimidine derivatives, pyrazole derivatives, pyrazolopyrimidine derivatives, or physiologically acceptable salts thereof. Preferred pyrimidine derivatives are 2,4,5,6-tetraaminopyrimidine, 4-hydroxy-2,5,6-triaminopyrimidine, and physiologically acceptable salts thereof. A preferred pyrazole derivative is 4,5-diamino-1-(2-hydroxyethyl)pyrazole and physiologically acceptable salts thereof. Pyrazolo[1,5-a]pyrimidine is particularly preferred as a pyrazolopyrimidine.

Preferred oxidation dye precursors of the developer type are selected from the group consisting of p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl) methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-amino-methylphenol, 4-amino-2-(1,2-dihydroxyethyl)phenol, and 4-amino-2-(diethylaminomethyl)phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, or the physiologically acceptable salts of these compounds.

Especially preferred developer components are p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl] amine, and/or 4,5-diamino-1-(2-hydroxyethyl) pyrazole.

According to another preferred embodiment of the present invention, the cosmetic agent according to the present invention further includes additionally at least one coupler component, in addition to the at least one developer component, as an oxidation dye precursor. m-Phenylenediamine derivatives, naphthols, resorcinol and resorcinol derivatives, pyrazolones, and m-aminophenol derivatives are generally used as coupler components.

Coupler components that are preferred according to the present invention are selected from:
a) m-aminophenol and derivatives thereof, in particular 3-aminophenol, 5-amino-2-methylphenol, 3-amino-2-chloro-6-methylphenol, 5-amino-4-chloro-2-methylphenol, 5-(2'-Hydroxyethyl) amino-2-methylphenol, and 2,4-dichloro-3-aminophenol;
b) o-aminophenol and derivatives thereof, such as 2-amino-5-ethylphenol;
c) m-diaminobenzene and derivatives thereof, such as, for example, 2,4-diaminophenoxyethanol, 1,3-bis-(2', 4'-diaminophenoxy) propane, 1-methoxy-2-amino-4-(2'-hydroxyethylamino) benzene, 2,6-bis-(2'-hydroxyethylamino)-1-methylbenzene, 2-({3-[(2-hydroxyethyl)amino]-4-methoxy-5-methylphenyl}amino) ethanol, and 2-({3-[(2-hydroxyethyl) amino]-2-methoxy-5-methylphenyl}-amino) ethanol;
d) o-diaminobenzene and derivatives thereof;
e) di- or trihydroxybenzene derivatives, in particular resorcinol, 2-chlororesorcinol, 4-chlororesorcinol, 2-methylresorcinol, and 1,2,4-trihydroxybenzene;
f) pyridine derivatives, in particular 3-amino-2-methylamino-6-methoxypyridine, 2,6-diaminopyridine, 2,6-dihydroxy-3,4-dimethylpyridine, 2-amino-3-hydroxypyridine, and 3,5-diamino-2,6-dimethoxy-pyridine;
g) naphthalene derivatives, such as 1-naphthol and 2-methyl-naphthol;
h) morpholine derivatives, such as 6-hydroxybenzomorpholine;
i) quinoxaline derivatives;
j) pyrazole derivatives, such as 1-phenyl-3-methylpyrazol-5-one;
k) indole derivatives, such as 6-hydroxyindole;
l) pyrimidine derivatives; or m) methylenedioxybenzene derivatives, such as 1-(2'-hydroxyethyl)-amino-3,4-methylendioxybenzene and physiologically acceptable salts thereof.

Coupler components that are preferred according to the present invention are selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)-amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or physiologically acceptable salts of the aforementioned compounds.

Coupler components that are preferred according to the present invention are resorcinol, 2-methylresorcinol, 4-chlororesorcinol, 5-amino-2-methylphenol, 3-aminophenol, 2-(2,4-diaminophenoxy) ethanol, 1,3-bis-(2,4-diaminophenoxy) propane, 1-methoxy-2-amino-4-(2'-hydroxyethylamino) benzene, 2-amino-3-hydroxypyridine, 2,6-dihydroxy-3,4-dimethylpyridine, 1,5-dihydroxynaphthalene, 2,7-dihydroxynaphthalene, and 1-naphthol, and physiologically acceptable salts thereof.

In an especially preferred embodiment of the present invention, the cosmetic agents according to the present invention are characterized by containing, as an oxidation dye precursor, at least one developer component selected from the group consisting of p-phenylenediamine, p-tolylenediamine, N,N-bis-(2-hydroxyethyl) amino-p-phenylenediamine, 1,3-bis-[(2-hydroxyethyl-4'-aminophenyl) amino]-propan-2-ol, 1,10-bis-(2',5'-diaminophenyl)-1,4,7,10-tetraoxadecane, 4-aminophenol, 4-amino-3-methylphenol, bis-(5-amino-2-hydroxyphenyl)methane, 2,4,5,6-tetraaminopyrimidine, 2-hydroxy-4,5,6-triaminopyrimidine, 4,5-diamino-1-(2-hydroxyethyl)pyrazole, physiologically acceptable salts thereof, and mixtures thereof, and at least one coupler component selected from the group consisting of resorcinol, 2-methylresorcinol, 5-methyl-resorcinol, 2,5-dimethylresorcinol, 4-chlororesorcinol, resorcinol monomethyl ether, 5-aminophenol, 5-amino-2-methylphenol, 5-(2-hydroxyethyl)amino-2-methylphenol, 3-amino-4-chloro-2-methylphenol, 3-amino-2-chloro-6-methylphenol, 3-amino-2,4-dichlorophenol, 2,4-diaminophenoxyethanol, 2-amino-4-(2'-hydroxyethyl)amino anisole sulfate, 1,3-bis-(2,4-diaminophenoxy)propane, 2-amino-3-hydroxypyridine, 2-methylamino-3-amino-6-methoxypyridine, 2,6-dihydroxy-3,4-dimethylpyridine, 3,5-diamino-2,6-dimethoxypyridine, 1-naphthol, 2-methyl-1-naphthol, 1,5-dihydroxynaphthalene, 2,7-dihydroxynaphthalene, 1-phenyl-3-methylpyrazol-5-one, 2,6-bis-[(2'-hydroxyethyl) amino] toluene, 4-hydroxyindole, 6-hydroxyindole, 6-hydroxybenzomorpholine, physiologically acceptable salts thereof, and mixtures thereof.

In order to obtain balanced and subtle shading, it may also be provided within the framework of the present invention that the cosmetic agents according to the present invention additionally include at least one direct dye. Direct dyes are dyes that are taken directly up into the hair and do not require an oxidative process to form the color. Direct dyes are typically nitrophenylenediamines, nitroaminophenols, azo dyes, anthraquinones, or indophenols.

Direct dyes can be divided into anionic, cationic, and nonionic direct dyes.

Preferred anionic direct dyes are the compounds known under the designations Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, and Tetrabromphenol blue. Preferred cationic direct dyes are cationic triphenylmethane dyes, such as Basic Blue 7, Basic Blue 26, Basic Violet 2, and Basic Violet 14, and aromatic systems substituted with a quaternary nitrogen group such as Basic Yellow 57, Basic Red 76, Basic Blue 99, Basic Brown 16, and Basic Brown 17, and HC Blue 16, as well as Basic Yellow 87, Basic Orange 311, and Basic Red 51. Preferred nonionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, and Disperse Black 9, and 1,4-diamino-2-nitrobenzene, 2-amino-4-nitrophenol, 1,4-bis-(2-hydroxyethyl) amino-2-nitrobenzene, 3-nitro-4-(2-hydroxyethyl) aminophenol, 2-(2-hydroxyethyl) amino-4,6-dinitrophenol, 4-[(2-hydroxyethyl) amino]-3-nitro-1-methylbenzene, 1-amino-4-(2-hydroxyethyl) amino-5-chloro-2-nitrobenzene, 4-amino-3-nitrophenol, 1-(2'-ureidoethyl) amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and chloro-6-ethylamino-4-nitrophenol.

Furthermore, as direct dyes, it is also possible to use naturally-occurring dyes, such as are included, for example, in henna red, henna neutral, henna black, chamomile flower, sandalwood, black tea, walnut, alder buckthorn bark, sage, logwood, madder root, catechu, and alkanet.

Preferably, the cosmetic agent according to the present invention includes the direct dyes in a total amount of 0.001 to 10 wt %, preferably 0.01 to 8 wt %, preferably 0.1 to 5 wt %, in particular 0.5 to 3 wt % relative to the total weight of the cosmetic agent.

As a second essential component b), the cosmetic agents according to the present invention include at least one specific protein-siloxane polymer. The specific protein-siloxane polymer used within the framework of the present invention has sufficient stability to different pH values and strongly-oxidizing substances, and therefore ensures improved care for the keratinous fibers, even under harsh chemical conditions that occur during an oxidative hair coloration. Due to the high stability of the protein-siloxane polymer used according to the present invention, excellent storage stability of the cosmetic agents according to the present invention is ensured.

According to a preferred embodiment of the present invention, in the structural unit of formula (I), X stands for the group *—CH2—CH(OH)—CH2—O—(CH2)3—*, R1 and R2 each stand for a hydroxy group, and R3 stands for a hydrogen atom.

Furthermore, it is preferred according to the present invention when, in the structural unit of formula (II), X stands for the group *—CH2—CH(OH)—CH2—O—(CH2)3—*, R1 and R2 each stand for a hydroxy group, and R3 stands for a hydrogen atom.

Especially preferably according to the present invention, the cosmetic agent includes at least one protein-siloxane polymer containing at least one structural unit of formula (IV) and/or at least one structural unit of formula (V).

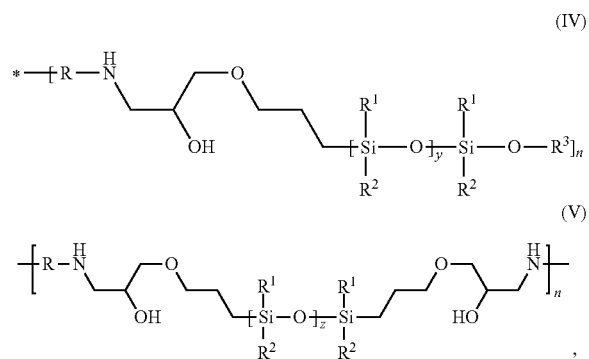

where:
R stands for a hydrolyzed protein residue having at least one NH2 group;
R1 and R2 each independently of one another stand for a methyl group, a hydroxy group, an alkoxy group having 1 to 6 carbon atoms in the alkyl chain, a residue of formula (VIa)

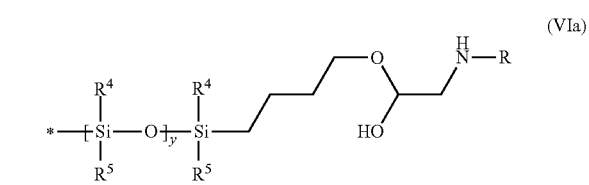

or (VIb)

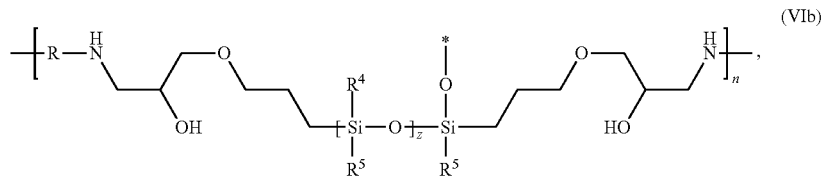

where R4 and R5 each independently of one another stand for a methyl group, a hydroxy group, or an alkoxy group having 1 to 6 carbon atoms in the alkyl chain;
R3 stands for a hydrogen atom or a group *—CH2—CH(OH)—CH2—O—(CH2)3—H,
n stands for an integer 1 to 101, and
y stands for an integer 0 to 1,000, preferably 0 to 500, in particular 0 to 100; and
z stands for an integer 1 to 1,000, preferably 1 to 500, in particular 1 to 100.

The use of these specific protein-siloxane polymers results in enhanced care for the keratinous fibers, in particular enhanced wet combability, after the color of the keratinous fibers has been altered. At the same time, these protein-siloxane polymers have sufficient stability to the oxidizing agents used for oxidative dyeing, so that no decomposition of these molecules occurs during the oxidative hair coloration. In addition, these protein-siloxane polymers are in no way incompatible with the ingredients typically used in oxidative dyes, so that the cosmetic agents according to the present invention have excellent storage stability.

The protein-siloxane polymers that are used according to the present invention—in particular, the polymers according to the structural formulae (I), (II), (IV), and (V)—can be obtained by reacting an organofunctional silicon having at least one reactive group selected from acyl halides, sulfonyl halides, anhydrides, aldehydes, and epoxy groups with a protein residue. As reactive silicon components, any compounds containing a siloxane group (Si—O—Si) or a silane group—which can form siloxanes through condensation—may be used. Crosslinked protein-siloxane polymers are preferable to use according to the present invention. The crosslinking may be performed either by using polyfunctional silicon compounds or by using monofunctional silicon compounds having at least one free silanol group (Si—OH).

Within the framework of this embodiment, it is especially preferred when, in the structural unit of formula (IV) and/or in the structural unit of formula (V), X stands for the group *—CH2—CH(OH)—CH2—O—(CH2)3—*, R1 and R2 each stand for a hydroxy group, and R3 stands for a hydrogen atom.

Preferably, the at least one protein-siloxane polymer b) includes 0.1 to 0.4, in particular 0.1 to 0.3 molecules of siloxane per amino group of the hydrolyzed protein residue R. Especially favorable care effects are obtained when the protein-siloxane polymer has the aforementioned ratio. This ratio may be obtained by using the corresponding stoichiometry of the protein residue to the organofunctional silicon compound. For this purpose, first, the free amino groups of the protein are determined, for example, with the use of 2,4,6-trinitrobenzenesulfonic acid as a determination reagent (see Fields R., Biochem. J., 1971, 124, 581-590), from which the required amount of the organofunctional silicon compound for adjusting the above ratios is determined.

It has furthermore proven advantageous when the at least one protein-siloxane polymer b) includes 5 to 30%, preferably 5 to 25%, preferably 10 to 30%, in particular 10 to 15% amine groups reacted with siloxanes, and 70 to 95%, preferably 75 to 95%, preferably 80 to 95%, in particular 85 to 90% free amino groups. "Free amino groups" are understood to mean amino groups (NH2 groups) of the protein residue that have not been reacted with the organofunctional silicon compound and therefore exist as a free amino group or as a protonated amino group at corresponding pH values.

The free amino groups may be determined, for example, by means of the aforementioned methods. Protein-siloxane polymers having such amounts of free amino groups have proven especially effective in relation to intensifying the care effect of the cosmetic agents according to the present invention.

As the protein residue R, it is possible to consider essentially any protein that can be obtained from animal or plant sources, or by means of fermentation, and that is produced by chemical, in particular alkaline or acid hydrolysis, through enzymatic hydrolysis, and/or through a combination of both types of hydrolysis. All hydrolytically active enzymes, e.g., proteases, are suitable for the enzymatic degradation. Overviews of the production of protein hydrolysates can be found, for example, from G. Schuster and A. Domsch in Soaps, Oils, Fats, Waxes 108 (1982) 177 or Cosm. Toil. 99 (1984) 63, from H. W. Steisslinger in Parf. Kosm. 72 (1991) 556, and from F. Aurich et al. in Tens. Surf. Det. 29 (1992) 389. Within the framework of the present invention, mixtures of individual amino acids obtained only by mixing the pure substances of the amino acids or total hydrolysates composed solely of individual amino acids do not fall under the terms "hydrolyzed protein" or "protein hydrolysate."

It is therefore preferable according to the present invention when the hydrolyzed protein residue R is a vegetable protein hydrolysate, preferably a protein hydrolysate isolated from the genus Solanum, in particular a protein hydrolysate isolated from the potato. The genus with the Latin name Solanum designates the nightshades, e.g., the potato, the pepper, the tomato, and the like. Especially favorable results within the framework of the present invention are obtained, however, when protein hydrolysates that can be isolated from the potato are used. Protein hydrolysates from the potato that can be used according to the present invention can be obtained, for example, under the trade name Hydrosolanum from Croda, and have average molecular weights Mw of around 750 Da.

According to a preferred embodiment of the present invention, the hydrolyzed protein residue R has a mean molecular weight Mw of 295 to 40,000 Da, preferably 295 to 35,000 Da, preferably 295 to 30,000 Da, in particular 295 to 26,000 Da. Protein-siloxane polymers that have hydrolyzed protein residues with the aforementioned average molecular weights Mw lead to an especially good care for the keratinous fibers dyed with the cosmetic agents according to the present invention. The average molecular weight Mw can be determined, for example, by gel permeation chromatography (GPC) (Andrews P.; "Estimation of the Molecular Weights of Proteins by Sephadex Gel-Filtration"; Biochem. J., 1964, 91, pp. 222-233).

Furthermore, within the framework of the present invention, it is advantageous when the at least one protein-siloxane polymer b) has an average molecular weight Mw of 350 to 90,000 Da, preferably 600 to 80,000 Da, preferably 1,000 to 70,000 Da, in particular 2,000 to 64,000 Da. Specific protein-siloxane polymers that have the aforementioned average molecular weight Mw result in an especially good care for keratinous fibers after the color alteration. The mean molecular weight Mw can be determined, for example, by gel permeation chromatography (GPC) (Liu X. M. et. al.; "Comparative Studies of Poly(DimethylSiloxanes) Using Automated GPC-MALDI-TOF MS and On-Line GPC-ESI-TOF MS"; Am. Soc. Mass. Spectrom., 2003, 14, pp. 195-202).

The at least one protein-siloxane polymer b) is included in the cosmetic agents according to the present invention in a total amount of 0.00002 to 4.0 wt %, preferably 0.0001 to 2.0 wt %, preferably 0.0002 to 1.0 wt %, further preferably 0.01 to 0.4 wt %, in particular 0.02 to 0.2 wt %, relative to the total weight of the cosmetic agent. The use of the aforementioned total amount of the specific protein-siloxane polymer leads to an enhanced care for the keratinous fibers and, at the same time, ensures high storage stability for the cosmetic agents according to the present invention, because at these total amounts, no undesired interactions with other ingredients of the cosmetic agents occur.

It has been shown that adding unfunctionalized protein hydrolysates is especially advantageous within the framework of the present invention. Cosmetic agents that are preferred according to the present invention therefore additionally include at least one unfunctionalized protein hydrolysate, preferably an unfunctionalized protein hydrolysate isolated from the genus Solanum, in particular an unfunctionalized protein hydrolysate isolated from the potato. The term "unfunctionalized protein hydrolysate" is understood according to the present invention to mean a protein hydrolysate that has been subjected, after hydrolysis and optionally purification, to no other modification, in particular to no chemical and/or physical modification. Adding the at least one unfunctionalized protein hydrolysate makes it possible to further enhance the care effect of the cosmetic agents according to the present invention.

The cosmetic agents according to the present invention may include additional active ingredients and additives. It is therefore preferred within the framework of the present invention when the cosmetic agent additionally includes at least one additional compound selected from the group consisting of: (i) thickening agents; (ii) linear or branched saturated or unsaturated alcohols having 8 to 20 carbon atoms; (iii) surfactants, in particular amphoteric surfactants; (iv) alkalizing agents; (v) oils; and (vi) mixtures thereof.

Preferably, the cosmetic agents according to the present invention are formulated as flowable preparations. Then, the cosmetic agents according to the present invention should be formulated so as to be readily applied to and spread on the site of application, on the one hand, and yet, on the other hand, so as to be sufficiently viscous so as to stay at the site of action and not run during the exposure time.

It has therefore been proven to be advantageous according to the present invention when the cosmetic agents according to the present invention include at least one thickening agent selected from the group consisting of (i) anionic, synthetic polymers; (ii) cationic, synthetic polymers; (iii) naturally occurring thickening agents such as nonionic guar gum, scleroglucan gum or xanthan gum, gum arabic, ghatti gum, karaya gum, tragacanth gum, carrageenan gum, agar, locust bean gum, pectins, alginates, starch fractions and derivatives such as amylose, amylopectin, and dextrins, and also cellulose derivatives, for example methylcellulose, carboxyalkylcelluloses, and hydroxyalkyl celluloses; (iv) nonionic, synthetic polymers such as polyvinyl alcohol or polyvinylpyrrolidinone; (v) inorganic thickening agents, in particular phyllosilicates, for example bentonite, especially smectites, such as montmorillonite or hectorite; and (vi) mixtures thereof, in a total amount of 0.0005 to 5.0 wt %, preferably 0.001 to 3.0 wt %, preferably 0.005 to 1.0 wt %, in particular 0.008 to 0.01 wt %, relative to the total weight of the cosmetic agent.

It has proven especially advantageous within the framework of the present invention when, as a thickening agent, at least one naturally-occurring thickening agent—in particular xanthan gum and salts thereof—is included in a total amount of 0.0005 to 5.0 wt %, preferably 0.001 to 1.0 wt %, preferably 0.005 to 0.5 wt %, in particular 0.01 to 0.1 wt %, relative to the total weight of the cosmetic agent.

Within the framework of the present invention, it may be preferably when the linear or branched saturated or unsaturated alcohol having 8 to 20 carbon atoms is selected from the group consisting of myristyl alcohol (1-tetradecanol), stearyl alcohol (1-octadecanol), cetearyl alcohol, 2-octyldodecanol, arachyl alcohol (eicosan-1-ol), gadoleyl alcohol ((9Z)-icos-9-en-1-ol), arachidone alcohol ((5Z,8Z,11Z,14Z)-eicosa-5,8,11,14-tetraen-1-ol), preferably 2-octyldodecanol and/or cetearyl alcohol, and included in a total amount of 1.0 to 35 wt %, preferably 5.0 to 30 wt %, preferably 10 to 25 wt %, in particular 12 to 20 wt %, relative to the total weight of the cosmetic agent.

Preferably, the cosmetic agents according to the present invention may furthermore include at least one partial ester of a polyol having 2 to 6 carbon atoms and linear, saturated carboxylic acids having 12 to 30, in particular 14 to 22 carbon atoms, wherein the partial esters may be hydroxylated, in a total amount of 0.5 to 10 wt %, in particular 3.0 to 8.0 wt %, relative to the total weight of the cosmetic agent. Such partial esters are, in particular: monoesters and diesters of glycerol; monoesters of propylene glycol; monoesters and diesters of ethylene glycol; monoesters, diesters, triesters, and tetraesters of pentaerythritol, each comprising linear saturated C12-C30 carboxylic acids, which may be hydroxylated, in particular those with palmitic and stearic acid; sorbitan monoesters, diesters, or triesters of linear saturated C12-C30 carboxylic acids, which may be hydroxylated, especially those of myristic acid, palmitic acid, stearic acid; or mixtures of these fatty acids, and the methyl glucose monoesters and diesters of linear saturated C12-C30 carboxylic acids, which may be hydroxylated.

Within the framework of the present invention, it may be provided that the cosmetic agents according to the present invention include at least one polyol partial ester selected from glycerol monostearate, glycerol monopalmitate, glycerol distearate, glycerol dipalmitate, ethylene glycol monostearate, ethylene glycol monopalmitate, ethylene glycol distearate, ethylene glycol dipalmitate, and mixtures thereof, in particular mixtures of glycerol monostearate, glycerol monopalmitate, glycerol distearate, and glycerol dipalmitate, in a total amount of 0.5 to 10 wt %, in particular 3.0 to 8.0 wt %, relative to the total weight of the cosmetic agent.

The use of the aforementioned alcohols, partial esters, and (poly)partial esters in the cosmetic agents according to the present invention may be especially preferred, then, when the cosmetic agents according to the present invention exist in the formula of an oil-in-water emulsion.

Furthermore, it may be provided according to the present invention that the cosmetic agents according to the present invention include at least one surfactant. Surfactants within the meaning of the present invention are amphiphilic (bi-functional) compounds composed of at least one hydrophobic moiety and at least one hydrophilic moiety. A basic property of surfactants and emulsifiers is the oriented absorption at the interfaces, as well as aggregation into micelles and the formation of lyotropic phases.

According to a preferred embodiment of the present invention, the cosmetic agents according to the present invention include at least one amphoteric surfactant in a total amount of 0.1 to 5.0 wt %, in particular 0.2 to 2.0 wt %, relative to the total weight of the cosmetic agent. Amphoteric or zwitterionic surfactants refer to those surface-active compounds that have at least one quaternary ammonium group and at least one —COOH— or —SO3(-) group.

The following compounds are especially preferred as amphoteric surfactants within the framework of the present invention:
  alkyl betaines having 8 to 20 carbon atoms in the alkyl group,
  amidopropyl betaines having 8 to 20 carbon atoms in the acyl group,
  sulfobetaines having 8 to 20 carbon atoms in the acyl group, and
  amphoacetates or amphodiacetates having 8 to 20 carbon atoms in the acyl group.

In an especially preferred embodiment, the cosmetic agents according to the present invention include, as a surfactant, at least one amphoteric surfactant selected from amidopropyl betaines having 9 to 13 carbon atoms in the acyl group, in a total amount of 0.1 to 5.0 wt %, in particular 0.2 to 2.0 wt %, relative to the total weight of the cosmetic agent.

It may, furthermore, be provided that the cosmetic agents according to the present invention include at least one ethoxylated nonionic surfactant in a total amount of 0.5 to 6.0 wt %, in particular 1.0 to 4.0 wt %, relative to the total weight of the cosmetic agent. Then, it has proven especially advantageous when the ethoxylated nonionic surfactant has an HLB value above 10, preferably above 13. So doing requires the nonionic surfactant to have a sufficiently high degree of ethoxylation. In this context, the cosmetic agent according to the present invention therefore includes, as an ethoxylated nonionic surfactant, at least one ethoxylated surfactant having at least 12 ethylene oxide units. In addition to the correspondingly ethoxylated fatty alcohols—in particular lauryl alcohol, myristyl alcohol, cetyl alcohol, stearyl alcohol, arachyl alcohol, and behenyl alcohol—the addition products of 20 to 60 mol ethylene oxide with castor oil and hydrogenated castor oil are especially suitable according to the present invention. The at least one ethoxylated nonionic surfactant is preferably selected from surfactants under the INCI designations Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, as well as mixtures of these substances, especially preferably selected from Ceteth-20, Steareth-20, Ceteareth-20, Ceteth-30, Steareth-30, and Ceteareth-30.

Cosmetic agents within the framework of the present invention generally have an alkaline pH value, in particular between pH 8.0 and pH 12. These pH values are required in order to ensure opening of the outer cuticle layer and allow the oxidation dye precursors and/or oxidizing agent to penetrate into the hair.

The aforementioned pH value may preferably be adjusted with the use of an alkalizing agent. Within the framework of the present invention, the alkalizing agent is selected from the group consisting of (i) inorganic alkalizing agents, (ii) organic alkalizing agents, and (iii) mixtures thereof, and in a total amount of 1.5 to 9.5 wt %, preferably 2.5 to 8.5 wt %, preferably 3.0 to 8.0 wt %, in particular 3.5 to 7.5 wt %, relative to the total weight of the cosmetic agent.

Preferred inorganic alkalizing agents are selected from the group consisting of ammonia, ammonium hydroxide, i.e., aqueous solutions of ammonia, sodium hydroxide, potassium hydroxide, calcium hydroxide, barium hydroxide, sodium phosphate, potassium phosphate, sodium silicate, potassium silicate, sodium carbonate, and potassium carbonate, and mixtures thereof. Ammonia or ammonium hydroxide is an especially preferred alkalizing agent. Particularly preferably, ammonia is included in a total amount of 0.1 to 20 wt %, preferably 0.5 to 10 wt %, in particular 1.0 to 7.0 wt %, relative to the total weight of the cosmetic agent.

Preferred organic alkalizing agents are selected from at least one alkanolamine. Organic alkalizing agents that are preferred according to the present invention are selected from alkanolamines of primary, secondary, or tertiary amines with a C2-C6 alkyl parent substance bearing at least one hydroxy group. Preferred alkanolamines are selected from the group consisting of 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino -2-methylpropan-2-ol, 3-aminopropane-1,2-diol, 2-amino-2-methylpropane-1,3-diol, 2-amino-2-ethyl-1,3-propanediol, N,N-dimethylethanolamine, triethanolamine, diethanolamine, and triisopropanolamine. Alkanolamines that are very especially preferred according to the present invention are selected from the group consisting of 2-aminoethan-1-ol (monoethanolamine), 2-amino-2-methylpropan-1-ol, 2-amino-2-methyl-propan-1,3-diol, and triethanolamine. Especially preferred cosmetic agents according to the present invention include a mixture of monoethanolamine and 2-amino-2-methylpropan-1-ol. Preferably, the at least one alkanolamine is included in a total amount of 0.05 to 15 wt %, preferably 0.5 to 10 wt %, in particular 3.5 to 7.5 wt %, relative to the total weight of the cosmetic agent.

Further organic alkalizing agents that are preferred according to the present invention are selected from alkaline amino acids, especially preferably selected from the group consisting of L-arginine, D-arginine, D/L-arginine, L-lysine, D-lysine, D/L-lysine, and mixtures thereof. Alkaline amino acids that are especially preferred according to the present invention are selected from L-arginine, D-arginine, and D/L-arginine. Preferred cosmetic agents according to the present invention include at least one alkalizing agent that is different from alkanolamines and ammonia, in a total amount of 0.05 to 5.0 wt %, in particular 0.5 to 3.0 wt %, relative to the total weight of the cosmetic agent.

Preferably according to the present invention, the alkalizing agent is selected from the group consisting of sodium hydroxide, potassium hydroxide, ammonia, monoethanolamine, and 2-amino-2-methylpropane, preferably monoethanolamine, and is included in a total amount of 1.5 to 9.5 wt %, preferably 2.5 to 8.5 wt %, preferably 3.0 to 8.0 wt %, in particular 3.5 to 7.5 wt %, relative to the total weight of the cosmetic agent.

In an especially preferred embodiment, the cosmetic agents according to the present invention include, as the alkalizing agent, a mixture of at least two mutually different alkanolamines, in particular monoethanolamine and 2-amino-2-methylpropan-1-ol, in a total amount of 0.05 to 15 wt %, preferably 0.5 to 10 wt %, in particular 3.5 to 7.5 wt % relative to the total weight of the cosmetic agent.

Preferably, the pH value of the cosmetic agents according to the present invention, when measured at 22° C., is 8 to 13, preferably 9.5 to 12, preferably 10 to 11.5, in particular 10.5 to 11.

Within the framework of the present invention, it may furthermore be preferable when the cosmetic agents according to the present invention include at least one oil selected from the group consisting of sunflower oil, corn oil, soybean oil, pumpkin seed oil, grapeseed oil, sesame oil, hazelnut oil, apricot kernel oil, macadamia nut oil, arara oil, castor oil, avocado oil, and mixtures thereof, in a total amount of 0.1 to 10 wt %, preferably 0.2 to 5.0 wt %, in particular 0.5 to 2.0 wt %, relative to the total weight of the cosmetic agent. Adding at least one aforementioned oil makes it possible to further increase the care effect of the aminated silicon polymers.

Especially preferably, the cosmetic agents according to the present invention include grapeseed oil in a total amount of 0.1 to 10 wt %, preferably 0.2 to 5.0 wt %, in particular 0.5 to 2.0 wt % relative to the total weight of the cosmetic agent.

According to an especially preferred embodiment of the present invention, the cosmetic agents according to the present invention, which exist as an oil-in-water emulsion, contain—relative to the total weight of the cosmetic agents

- octyldodecanol in a total amount of 2.0 to 20 wt %, in particular 5.0 to 12 wt; and
- mixtures of glycerol monostearate, glycerol monopalmitate, glycerol distearate, and glycerol palmitate in a total amount of 0.5 to 10 wt %, preferably 3.0 to 8.0 wt %; and
- at least one amphoteric surfactant selected from amidopropyl betaines having 9 to 13 carbon atoms in the acyl group, in a total amount of 0.1 to 5.0 wt %, in particular 0.2 to 2.0 wt %; and
- a mixture of at least two mutually different alkanolamines, in particular monoethanolamine and 2-amino-2-methylpropan-1-ol, in a total amount of 0.05 to 15 wt %, preferably 0.5 to 10 wt %, in particular 3.5 to 7.5 wt %; and
- grapeseed oil in a total amount of 0.1 to 10 wt %, preferably 0.2 to 5.0 wt %, in particular 0.5 to 2.0 wt %.

The at least one protein-siloxane polymer that is preferably used according to the present invention may be obtained, for example, by reacting a hydrolyzed protein residue R with 1-[3-(2-oxiranylmethoxy)propyl]-silanetriol or 2-[[3-(trimethoxysilyl)propoxy]methyl]-oxirane. Producing crosslinked protein-siloxane polymers, in the case of 2-[[3-(trimethoxysilyl)propoxy]methyl]-oxirane, first requires hydrolysis of the methoxy groups, whereas crosslinking is possible without further hydrolysis reactions when 1-[3-(2-oxiranylmethoxy)propyl]-silanetriol is used. An oxirane that can be used within the framework of the present invention is, for example, commercially available under the trade name Silquest A187 from Momentive Inc. Another subject matter of the present invention is therefore a cosmetic agent for altering the color of keratinous fibers, comprising, in a cosmetically acceptable carrier,

- at least one compound selected from the group consisting of oxidation dye precursors, direct dyes, and mixtures thereof, and
- at least one protein-siloxane polymer of a hydrolyzed protein and 1-[3-(2-Oxiranylmethoxy)propyl]-silanetriol or 2-[[3-(Trimethoxysilyl)propoxy]methyl]-oxirane.

Within the framework of this subject matter of the present invention, it is preferable when the hydrolyzed protein is a vegetable protein hydrolysate, preferably a protein hydrolysate isolated from the genus Solanum, in particular a protein hydrolysate isolated from the potato. As previously stated, the use of protein-siloxane polymers containing protein hydrolysates isolated from the potato leads to improved care for keratinous fibers that have been dyed with the cosmetic agents according to the present invention.

Furthermore, within the framework of this subject matter of the present invention, it may be preferred when the hydrolyzed protein has an average molecular weight Mw of 295 to 40,000 Da, preferably 295 to 35,000 Da, preferably 295 to 30,000 Da, in particular 295 to 26,000 Da. The average molecular weight Mw of the hydrolyzed protein may be determined by means of the methods described in connection with the first subject matter of the present invention.

What has been said regarding the cosmetic agents according to the present invention also applies mutatis mutandis with respect to further embodiments of the subject matter of the present invention.

Oxidative dyes may also be produced immediately before use from two or more separately packed compositions. This is useful, in particular, for separating incompatible ingredients in order to avoid a premature reaction. Separation in multi-component systems is especially preferable where incompatibilities of the ingredients are to be expected or feared. The oxidative dye is, in these cases, produced by the consumer immediately before use, by mixing the components. Within the framework of the present invention, this procedure is especially preferred with oxidative dyes with which the cosmetic agent according to the present invention is first present separate from an oxidizing agent preparation containing at least one oxidizing agent.

Another subject matter of the present invention is therefore a packaging unit (kit-of-parts) comprising—prepared separately from one another—
at least one container (C1), containing a cosmetic agent according to the present invention; and
at least one container (C2) containing an oxidizing agent preparation containing, in a cosmetically acceptable carrier, at least one oxidizing agent in a total amount of 0.5 to 7.0 wt %, preferably 1.0 to 7.0 wt %, in particular 3.0 to 7.0 wt %, in particular relative to the total weight of the oxidizing agent preparation, and at least one acid.

The term "container" is understood within the framework of the present invention to mean a wrapping in the form of an (optionally re-sealable) bottle, a tube, a can, a sachet, or similar wrappings. No limitations are set according to the present invention for the wrapping material. Preferably, however, the wrapping is made of glass or plastic.

The oxidizing agents within the framework of the present invention are distinct from atmospheric oxygen. Hydrogen peroxide and solid addition products thereof with organic and inorganic compounds may be used as the oxidizing agent. In particular, the addition products of urea, melamine, polyvinyl pyrrolidone, and sodium borate may be considered solid addition products according to the present invention. Hydrogen peroxide and/or one of the solid addition products thereof with organic or inorganic compounds are especially preferable as oxidizing agents. Preferably according to the present invention, therefore, the oxidizing agent is selected from the group consisting of persulfates, chlorites, hydrogen peroxide, and addition products of hydrogen peroxide with urea, melamine, and sodium borate, in particular hydrogen peroxide.

An especially preferred embodiment of the present invention is thus characterized in that, as an oxidizing agent, hydrogen peroxide is included in a total amount of 0.5 to 7.0 wt %, preferably 1.0 to 7.0 wt %, in particular 3.0 to 7.0 wt %, relative to the total weight of the oxidizing agent preparation. The calculation of the total amount refers here to 100% H2O2.

The oxidizing agent preparations may furthermore include water in a total amount of 40 of 98 wt %, in particular 65 to 85 wt %, relative to the total weight of the oxidizing agent preparation.

According to a preferred embodiment of the present invention, the oxidizing agent preparations further include at least one linear saturated alkanol having 12 to 30 carbon atoms, in particular 16 to 22 carbon atoms, in a total amount of 0.1 to 10 wt %, preferably 0.5 to 5.0 wt %, in particular 1.0 to 4.0 wt % relative to the total weight of the oxidizing agent preparation. Especially preferred are cetyl alcohol, stearyl alcohol, arachidyl alcohol, behenyl alcohol, and lanolin alcohol, or mixtures of these alcohols, such as can be obtained from industrial hydrogenation of vegetable and animal fatty acids, as well as mixtures of these alcohols. The mixture cetearyl alcohol is especially preferred.

In another preferred embodiment of the present invention, the oxidizing agent preparations include at least one ethoxylated nonionic surfactant preferably selected from surfactants under the INCI designations Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, and mixtures of these substances, especially preferably selected from Ceteth-20, Steareth-20, Ceteareth-20, Ceteth-30, Steareth-30, and Ceteareth-30, in a total amount of 0.1 to 10 wt %, preferably 0.5 to 5.0 wt %, in particular 1 to 4.0 wt %, relative to the total weight of the oxidizing agent preparation.

Within the framework of the present invention, it may moreover also be provided that the oxidizing agent preparations include at least one ester of a carboxylic acid having 10 to 20 carbon atoms and a linear or branched alcohol having 1 to 5 carbon atoms, in particular isopropyl myristate, in a total amount of 3.0 to 25 wt %, preferably 5.0 to 20 wt %, in particular 8.0 to 15 wt %, relative to the total weight of the oxidizing agent preparation.

According to an especially preferred embodiment of the present invention, the oxidizing agent preparations contain—relative to the total weight of the oxidizing agent preparation—
at least one linear saturated alkanol having 12 to 30 carbon atoms in a total amount of 0.1 to 10 wt %, preferably 0.5 to 5.0 wt %, in particular 1.0 to 4.0 wt %; and
at least one ethoxylated nonionic surfactant, preferably selected from surfactants under the INCI designations Ceteth-12, Steareth-12, Ceteareth-12, Ceteth-20, Steareth-20, Ceteareth-20, Ceteth-30, Steareth-30, Ceteareth-30, Oleth-30, Ceteareth-50, PEG-40 Hydrogenated Castor Oil, and PEG-60 Hydrogenated Castor Oil, as well as mixtures of these substances, especially preferably selected from Ceteth-20, Steareth-20, Ceteareth-20, Ceteth-30, Steareth-30, and Ceteareth-30, in a total amount of 0.1 to 10 wt %, preferably 0.5 to 5.0 wt %, in particular 1.0 to 4.0 wt %; and
at least one ester of a carboxylic acid having 10 to 20 carbon atoms and a linear or branched alcohol having 1 to 5 carbon atoms, preferably isopropyl myristate, in a total amount of 3.0 to 25 wt %, preferably 5.0 to 20 wt %, in particular 8.0 to 15 wt %.

The oxidizing agent preparations according to the present invention further include at least one acid. Preferred acids are selected from: dipicolinic acid; edible acids such as citric acid, acetic acid, malic acid, lactic acid, and tartaric acid; diluted mineral acids such as hydrochloric acid, phosphoric acid, pyrophosphoric acid, and sulfuric acid; and mixtures thereof. The oxidizing agent preparations preferably have a pH value in the range of 2 to 5, in particular 3 to 4.

To produce oxidative dyes from the packaging unit (kit-of-parts) according to the present invention, the cosmetic agent according to the present invention in the container C1 is mixed with the oxidizing agent preparation in the container C2, or vice versa.

Furthermore, it may be advantageous according to the present invention when the packaging unit includes at least one additional hair treatment agent, in particular a conditioning agent preparation, in an additional container. This conditioning agent preparation advantageously includes at least one conditioning agent selected from the group consisting of cationic polymers, silicon derivatives, and oils. Moreover, the packaging unit may include application aids such as combs, brushes, applicators, or brushes, personal protective clothing—in particular disposable gloves—and optionally an instruction manual. An applicator is understood to mean a broad brush having, at the handle end thereof, a tip that makes it possible and easier to separate fiber bundles or small strands from the total quantity of fibers.

What has been said regarding the cosmetic agents according to the present invention also applies mutatis mutandis with respect to the cosmetic agent according to the present invention in the container C1 and the oxidizing agent preparation in the container C2.

Another subject matter of the present invention is a method for dyeing keratinous fibers, wherein the method comprises the following method steps:
preparing a cosmetic agent (M1) according to the present invention;
providing an oxidizing agent preparation (M2) containing, in a cosmetically acceptable carrier, at least one oxidizing agent in a total amount of 0.5 to 7.0 wt %, preferably 1.0 to 7.0 wt %, in particular 3.0 to 7.0 wt %, in particular relative to the total weight of the oxidizing agent preparation, and at least one acid;
mixing the cosmetic agent (M1) with the oxidizing agent preparation (M2);
applying the mixture obtained in step c) to the keratinous fibers and leaving this mixture on the keratinous fibers for a duration of 10 to 60 minutes, preferably 20 to 45 minutes, at room temperature and/or at least 30° C.;
rinsing the keratinous fibers with water and/or a cleansing composition for 1 to 5 minutes; and
optionally applying a post-treatment agent to the keratinous fibers and rinsing out after a duration of 1 to 10 minutes.

The method according to the present invention for dyeing keratinous fibers with the use of a specific protein-siloxane polymer results in improved care for dyed keratinous fibers.

Room temperature is understood within the framework of the present invention to mean the surrounding ambient temperature that prevails without exposure to external heat and preferably amounts to 10° C. to 39° C. The action of the dye composition may be intensified by external heat supply, for example, by means of a heating hood. The preferred exposure time of the dye composition to the keratinous fibers is 10 to 60 min., preferably 20 to 45 min. After termination of the exposure time, the remaining dye is washed out from the keratinous fibers with the aid of a cleaning preparation—which preferably includes at least one cationic and/or anionic and/or nonionic surfactant—and/or water. Optionally, the process is repeated with another means. After the washing out, the keratinous fibers are optionally rinsed with a post-treatment agent, e.g., a conditioning agent, and dried with a towel or a hot air blower. The dye composition is usually applied manually by the user. It is then preferable to wear protective clothing, in particular suitable protective gloves, e.g., made of plastic or latex, for single use (disposable gloves), and optionally an apron. It is, however, also possible to apply the dyes to the keratinous fibers with an application aid.

Especially preferred methods according to the present invention are characterized in that the methods result in improved care for the keratinous fibers. The use of at least one specific protein-siloxane polymer makes it possible for the method according to the present invention to result in a greater care effect than the care effect that can be achieved in the absence of the protein-siloxane polymer b) that is used according to the present invention.

What has been said about the cosmetic agents according to the present invention and the packaging unit according to the present invention applies, mutatis mutandis, to the cosmetic agent M1 according to the present invention, the oxidizing agent preparation M2, and further preferred embodiments of the method according to the present invention.

In addition, another subject matter of the present invention is the use of a cosmetic agent according to the present invention to enhance the care of keratinous fibers. The use of a specific protein-siloxane polymer results in enhanced care for dyed keratinous fibers.

What has been said about the cosmetic agents according to the present invention and the packaging unit according to the present invention applies, mutatis mutandis, to further preferred embodiments of the use according to the present invention.

In addition, another subject matter of the present invention is the use of a packaging unit according to the present invention to produce a cosmetic agent for altering the color of keratinous fibers with enhanced care for the keratinous fibers. The use of a specific protein-siloxane polymer results in enhanced care for dyed keratinous fibers.

What has been said about the cosmetic agents according to the present invention and the packaging unit according to the present invention applies, mutatis mutandis, to further preferred embodiments of the use according to the present invention.

The following examples are intended to reveal preferred embodiments of the present invention, but without limiting same.

EXAMPLES

1. Formulations

Compositions of the used cosmetic agents (oil-in-water emulsions, all amounts in wt %). The protein-siloxane polymer used in the following formulations is preferably a protein-siloxane polymer of formula (IV) and/or (V) with R1 and R2, each independently of one another, methyl and/or a residue (VIa) or (VIb), and an average molecular weight Mw of 2,000 to 64,000 Da.

| Raw material | V1 | E1* | E2* |
|---|---|---|---|
| Xanthan gum | 0.05 | 0.05 | 0.05 |
| 2-Octyldodecanol | 2.3 | 2.3 | 2.3 |
| Lanette N $^{a)}$ | 14 | 14 | 14 |
| Cetearyl Alcohol | 3.9 | 3.9 | 3.9 |
| Glycerol monostearate | 6.0 | 6.0 | 6.0 |
| Glycerol 99.5% | 2.0 | 2.0 | 2.0 |
| Cocoamidopropyl betaine, 40% | 2.0 | 2.0 | 2.0 |
| Monoethanolamine | 4.5 | 4.5 | 4.5 |
| 2-amino-2-methylpropanol | 0.1 | 0.1 | 0.1 |
| Sodium sulfite, anhydrous | 0.2 | 0.2 | 0.2 |
| Caramel syrup, 75% | 0.1 | 0.1 | 0.1 |

-continued

| Raw material | V1 | E1* | E2* |
|---|---|---|---|
| Grapeseed oil | 1.0 | 1.0 | 1.0 |
| p-toluenediamine sulfate | 0.03 | 0.03 | 0.03 |
| 4-amino-3-methylphenol | 0.3 | 0.3 | 0.3 |
| 1,3-Benzenediol | 0.04 | 0.04 | 0.04 |
| 1-Naphthol | 0.09 | 0.09 | 0.09 |
| 5-amino-2-methylphenol | 0.2 | 0.2 | 0.2 |
| 2-amino-6-chloro-4-nitrophenol | 0.2 | 0.2 | 0.2 |
| Protein-siloxane polymer ** | — | 0.21 | 0.42 |
| Water, deionized | to 100.00 | to 100.00 | to 100.00 |

*according to the present invention
** active substance
[a]) INCI designation: Cetearyl alcohol, Sodium cetearyl sulfate (BASF)

The fat base was in each case melted together at 80° C. and dispersed with a portion of the amount of water. Then, the remaining formulation components were incorporated in order under stirring, then filled to 100 wt % with water, and the formulation was stirred cold. The formulation V1 entails a comparison formulation not according to the present invention, without the protein-silicon polymer. The formulations E1 and E2 are examples according to the present invention.

Oxidizing agent preparation O1 (all amounts in wt %)

| Raw material | O1 |
|---|---|
| Disodium pyrophosphate | 0.10 |
| Dipicolinic acid | 0.10 |
| Potassium hydroxide 50% | 0.22 |
| 1-hydroxyethan-1,1-diphosphonic acid 60% | 0.25 |
| Emulgade F [b]) | 4.0 |
| Cetearyl Alcohol | 0.5 |
| Ceteareth-20 | 0.5 |
| Beeswax | 0.3 |
| Isopropyl myristate | 10 |
| Hydrogen peroxide, 50% | 11.2 |
| Water, deionized | to 100 |

[b]) INCI designation: Cetearyl alcohol, PEG-40 Castor oil, Sodium cetearyl sulfate (BASF)

2. Improved care through addition of at least one specific protein-siloxane polymer To produce the oxidative dyes for determining the care, the cosmetic agents V1, E1, and E2 were each mixed in a weight ratio of 1:1 with the above oxidizing agent preparation O1.

Twelve strands of naturally light-brown European hair (IHIP (New York), lot #03/2012, N104, length 15 cm, weight 1 g) were washed with an aqueous sodium lauryl ether sulfate solution (3% active substance content in the solution). The strands were air-dried and stored for 24 h at 25° C. and 25% relative air humidity. After these strands were soaked in water for 5 minutes, the wet combability thereof was determined (reference value).

For the colorations, 12 strands of natural European hair (IHIP (New York), lot #03/2012, N104, length 15 cm, weight 1 g) were respectively used with each oxidative dye. For this purpose, 4 g respectively of the previously produced oxidative dyes was applied per 1 g hair strands. After having been dyed for 30 min. at 32° C., the strands were rinsed with water for 2 min. and air-dried.

Wet combability was measured as follows:
Prior to measurement, each of the strands was moistened with water by combing with a hard, fine-toothed rubber comb (from Hercules Sägemann, Hamburg, Germany) for 2 seconds. After three combings, the combing strength was measured during an additional 10 combings, wherein each of the hair strands was slowly rotated during the combing. The resulting measurement values are compared with the use of the following statistical tests embedded in the software Statistica 10.0 (StatSoft Inc., USA):

Shapiro-Wilks test (test for normality) Outlier test according to Grubss
Bartlett Test (test on homoscedasticity of variances)
Univariant significance test
Newman-Keuls test (determination of significant differences)
Unequal N HSD test (test for multiple comparisons)

The change in the combing strength dK (in percent) can be calculated with the aid of the formula $dK=[(K0-Ki)/K0]*100$. K0 here is the mean value of the combing strength for the undyed hair strands, and Ki is the mean value for the hair strands that were treated with the respective oxidative dye.

The higher the care for the hair strands, the lower the combing strength applied and thus the higher the change in the combing strength. The following table represents the dK values for the colorations with the use of the cosmetic agents V1, E1, and E2. Colorations with the cosmetic agents E1 and E2 according to the present invention, which include at least one specific protein-siloxane polymer in a total amount of 0.21 wt %/0.42 wt %, have a higher change in comb force and thus enhanced care in comparison to the colorations without the protein-siloxane polymer (V1).

| Oxidative dye | dK [%] |
|---|---|
| V1 + O1 (1:1) | 21 |
| E1 + O1 (1:1) | 30 |
| E2 + O1 (1:1) | 26 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A cosmetic agent for altering the color or whitening of keratinous fibers, comprising, in a cosmetically acceptable carrier,
   a) at least one compound selected from the group consisting of oxidation dye precursors, direct dyes, and mixtures thereof,
   b) at least one protein-siloxane polymer that includes at least one structural unit of formula (I) and/or at least one structural unit of formula (II)

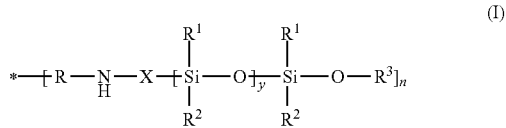

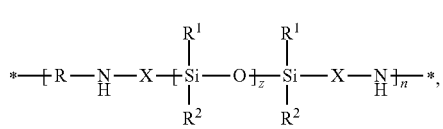
(II)

wherein R stands for a hydrolyzed protein residue having at least one NH2 group;
X stands for a group *—CH₂—CH(OH)—CH₂—O—(CH₂)₃—* or *—CO—CH(CH₂COOH)—CH—(CH₂)₃—*; R1 and R2 each independently of one another stand for a methyl group, a hydroxy group, an alkoxy group having 1 to 6 carbon atoms in the alkyl chain, a residue of formula (IIIa)

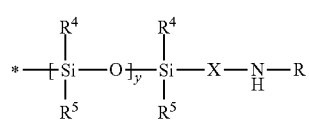
(IIIa)

or a residue of formula (IIIb)

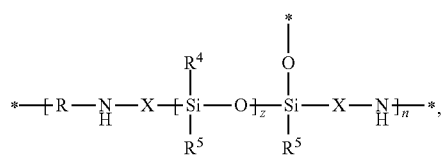
(IIIb)

wherein R4 and R5 each independently of one another stand for a methyl group, a hydroxy group, or an alkoxy group having 1 to 6 carbon atoms in the alkyl chain;
R3 stands for a hydrogen atom or a group X—H;
n stands for an integer 1 to 101;
y stands for an integer from 0 to 1,000; and
z stands for an integer from 1 to 1,000.

2. The cosmetic agent according to claim 1, wherein, in the structural unit of formula (I), X stands for the group *—CH₂—CH(OH)—CH₂—O—(CH₂)₃—*, R1 and R2 each stand for a hydroxy group, and R3 stands for a hydrogen atom.

3. The cosmetic agent according to claim 1, wherein, in the structural unit of formula (II), X stands for the group *—CH₂—CH(OH)—CH₂—O—(CH₂)₃—*, R1 and R2 each stand for a hydroxy group, and R3 stands for a hydrogen atom.

4. The cosmetic agent according to claim 1, wherein the cosmetic agent includes at least one protein-siloxane polymer containing at least one structural unit of formula (IV) and/or at least one structural unit of formula (V),

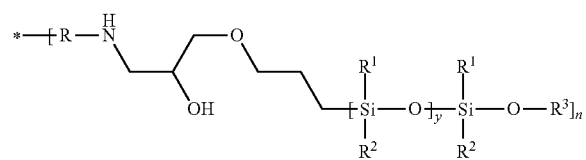
(IV)

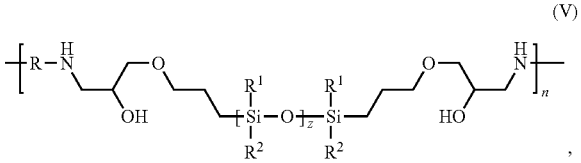
(V)

wherein:
R stands for a hydrolyzed protein residue having at least one NH2 group;
R1 and R2 each independently of one another stand for a methyl group, a hydroxy group, an alkoxy group having 1 to 6 carbon atoms in the alkyl chain, a residue of formula (VIa)

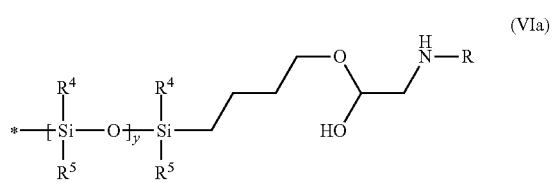
(VIa)

or a residue of formula (VIb)

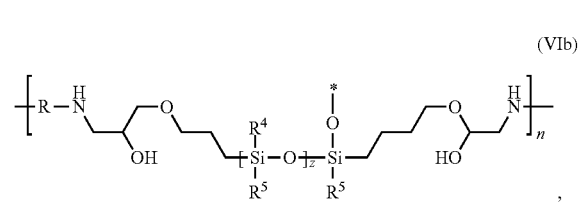
(VIb)

wherein R4 and R5 each independently of one another stand for a methyl group, a hydroxy group, or an alkoxy group having 1 to 6 carbon atoms in the alkyl chain;
R3 stands for a hydrogen atom or a group *—CH₂—CH(OH)—CH₂—O—(CH₂)₃—H,
n stands for an integer from 1 to 101,
y stands for an integer from 0 to 1,000; and
z stands for an integer from 1 to 1,000.

5. The cosmetic agent according to claim 1, wherein the at least one protein-siloxane polymer b) includes 0.1 to 0.4 molecules of siloxane per amino group of the hydrolyzed protein residue R.

6. The cosmetic agent according to claim 1, wherein the at least one protein-siloxane polymer b) includes 5 to 30% amine groups reacted with siloxanes, and 70 to 95% free amino groups.

7. The cosmetic agent according to claim 1, wherein the hydrolyzed protein residue R is a vegetable protein hydrolysate.

8. The cosmetic agent according to claim 7, wherein the hydrolyzed protein residue is a protein hydrolysate isolated from the potato.

9. The cosmetic agent according to claim 1, wherein the hydrolyzed protein residue R has an average molecular weight Mw of 295 to 40,000 Da.

10. The cosmetic agent according to claim 1, wherein the at least one protein-siloxane polymer b) has an average molecular weight Mw of 350 to 90,000 Da.

11. The cosmetic agent according to claim 1, wherein the cosmetic agent includes the at least one protein-siloxane polymer b) in a total amount of 0.00002 to 4.0 wt % relative to the total weight of the cosmetic agent.

12. The cosmetic agent according to claim 1, wherein the cosmetic agent further includes at least one unfunctionalized protein hydrolysate.

13. The cosmetic agent according to claim 12, wherein the at least one unfunctionalized protein hydrolysate includes an unfunctionalized protein hydrolysate isolated from the potato.

14. A packaging unit, otherwise known as a kit-of-parts, comprising —prepared separately from one another—
   a) at least one container (C1), containing the cosmetic agent according to claim 1; and
   b) at least one container (C2) containing an oxidizing agent preparation that includes, in a cosmetically acceptable carrier, at least one oxidizing agent in a total amount of 0.5 to 7.0 wt % relative to the total weight of the oxidizing agent preparation, and at least one acid.

15. A method for dyeing or whitening keratinous fibers, the method including:
   a) preparing the cosmetic agent (M1) according to claim 1;
   b) providing an oxidizing agent preparation (M2) containing, in a cosmetically acceptable carrier, at least one oxidizing agent in a total amount of 0.5 to 7.0 wt % relative to the total weight of the oxidizing agent preparation, and at least one acid;
   c) mixing the cosmetic agent (M1) with the oxidizing agent preparation (M2);
   d) applying the mixture obtained in step c) to the keratinous fibers and leaving this mixture on the keratinous fibers for a duration of 10 to 60 minutes at a temperature of at least 30° C.;
   e) rinsing the keratinous fibers with water and/or a cleansing composition for 1 to 5 minutes; and
   f) optionally applying a post-treatment agent to the keratinous fibers and rinsing out after a duration of 1 to 10 minutes.

* * * * *